United States Patent [19]

Heide et al.

[11] 4,039,445

[45] Aug. 2, 1977

[54] MATRIX OF ALGAE AND METHOD OF MAKING SAME AND METHOD OF OBTAINING URANIUM FROM SEA WATER BY SAID MATRIX

[75] Inventors: Erich-Alexander Heide; Maximilian Wald; Manfred Paschke; Klaus Wagener, all of Julich, Germany

[73] Assignee: Kernforschungsanlage Julich, Gesellschaft mit beschrankter Haftung, Julich, Germany

[21] Appl. No.: 674,109

[22] Filed: Apr. 6, 1976

Related U.S. Application Data

[63] Continuation of Ser. No. 504,493, Sept. 9, 1974, abandoned.

[30] Foreign Application Priority Data

Sept. 8, 1973 Germany .............................. 2345430
Aug. 30, 1974 Germany .............................. 2441479

[51] Int. Cl.$^2$ ............................................ B01D 15/00
[52] U.S. Cl. .................................... 210/38 C; 47/1.4;
47/DIG. 8; 252/180; 252/301.1 W; 423/6

[58] Field of Search ..................... 210/26, 38 B, 38 C, 210/2, 11, 3; 423/6; 252/301.1 R, 301.1 W, 180; 47/1.4, DIG. 8; 195/2

[56] References Cited

U.S. PATENT DOCUMENTS

| 3,650,068 | 3/1972 | Meyer et al. ............................. 47/1.4 |
| 3,721,533 | 3/1973 | Riedel ....................................... 423/6 |
| 3,725,291 | 4/1973 | Serbus et al. .......................... 210/24 |

OTHER PUBLICATIONS

Zlobin, V.S., "Uptake of U and Pu by Seaweeds"; Radiobiologiya, 6:613-7, (1966), abstracted in Nucl. Sc. Abstr. vol. 21, No. 13; 22372.

*Primary Examiner*—Thomas G. Wyse
*Assistant Examiner*—Benoit Castel
*Attorney, Agent, or Firm*—Walter Becker

[57] ABSTRACT

A matrix of algae mutants and method of obtaining thereby uranium from sea water, according to which a matrix is prepared of uranium compatible algae mutants suitable for picking up uranium dissolved in sea water, which matrix is then placed in an area of the sea in which low and high tides pass streams of sea water through the above mentioned matrix.

3 Claims, No Drawings

MATRIX OF ALGAE AND METHOD OF MAKING SAME AND METHOD OF OBTAINING URANIUM FROM SEA WATER BY SAID MATRIX

This is a continuation of application Ser. No. 504,493, filed Sept. 9, 1974, and now abandoned.

The present invention relates to a matrix consisting of algae, and a method of making such matrix as well as to the application of the matrix for obtaining from sea water uranium dissolved in sea water.

Numerous attempts have been made to obtain uranium from sea water because the sea water contains a practically unlimited supply of uranium. The heretofore known methods for obtaining uranium from sea water are based either on the principle of extraction in countercurrent or counterflow, on the chemical precipitation, addition, on the exchange of ions or on flotation. With all heretofore known methods of the type involved, it was, however, necessary to employ chemical substances. This has the drawback that in general great quantities of chemicals were needed so that the costs for the consumption of the respective materials were rather high and that pollution of the surroundings occurred which could not be eliminated at all or only at very high expenses. Another drawback inherent to these known methods consists in that a considerable consumption of energy was necessary to practice these heretofore known methods although uranium is present in sea water in great quantities, it occurs, however, in sea water in a very low concentration.

It is, therefore, an object of the present invention to provide a matrix and to employ the same for obtaining uranium from sea water without polluting the surroundings and without using any energy which requires relatively high expenses.

These objects have been realized according to the present invention by means of forming the above mentioned matrix from a uranium compatible mutant suitable for receiving uranium dissolved in sea water. In this connection it has proved particularly advantageous to employ a matrix which is formed of single-celled green algae, but it is to be understood that also multicelled algae are usable in this connection.

For the sake of completeness, it may be added that it is known that mutants of one-celled green algae are uranium compatible. It has also been speculated that such algae might be suitable for obtaining uranium from sea water but heretofore no teaching has been disclosed how to go about technically to realize this speculation.

A preferred method of practicing the present invention consists in that the matrix is arranged in a filter cage with at least two screen-shaped walls which permit sea water to pass through but which are non-permeable for the above mentioned mutants. The mesh size of the screen walls employed for the filter cages must be less than the size of the cells of the mutants forming the matrix. Therefore, the cell size of the algae forming the matrix should be around from 50 to 100 $\mu$.

For obtaining uranium compatible algae, green algae are in conformity with the present invention into a solution with a high uranium concentration which solution contains sea water or the essential components of sea water whereupon the thus obtained solution with the algae therein is subjected to radiation by X-rays. The remaining algae are sown on a uranium containing nutritive substream or nutrient medium, and the surviving cultures are taken off therefrom and are kept in pure sea water for forming a mass culture. In this connection it has proved expedient to introduce the algae in a sterilized solution adjusted to an acidity of pH6 of 3.8 grams sea salt, 0.03 grams of $NH_4NO_3$ as well as 5ml earth extracts in 100ml water. Thereupon uranium in the form of uranylnitrate is inserted stepwise into said solution until the quantity of uranium has been enriched to 250mg/1 whereupon as a further method step, the algae are subjected to radiation by X-rays the dose of which is approximately 50kR. The algae are then poured onto agar-plates which have been formed by the employment of a solution in 100ml water consisting of 3.8 grams of sea salt, 0.03 grams of $NH_4NO_3$ and 5ml earth extracts. In conformity with a further method step, the thus forming colonies are individually inoculated and are further cultivated in a nutritive solution of the above mentioned composition.

In order to obtain uranium from sea water, a flow of sea water is passed through the matrix formed according to the invention.

According to another modification according to the present invention for the obtainment of uranium from sea water, the matrix arranged in a filter cage is provided in an area of the sea which is subjected to the tides so that the flows of currents caused by the low tide and high tide are passed through filter cages surrounding the matrix. The total cross section of the matrix should in such an instance be approximately 100 square meters in order that with the flow velocity in the sea water as it is caused on an average by the tides generally in the vicinity of the shore will generate a through-flow rate through the cage of $10^6$t sea water per day. The separation of the uranium from the matrix is carried out by means of one of the customary methods for instance by extraction by means of tributylphosphate.

EXAMPLE

As starting materials, unicelled green algae were used which were derived from the sea water of the Mediterranean (LaEscala/Spain). These algae were introduced into a nutrient solution formed by a solution of 3.8 grams sea salt and 0.03 grams $NH_4NO_3$ in 100ml water. This solution was previously sterilized and subsequently was adjusted to an acidity of pH6. Furthermore, 5ml earth extracts were added to said solution. Subsequently uranium in the form of uranylnitrate was added to the solution while the addition of uranylnitrate was increased in steps up to a quantity of 250mg/1 uranium. The algae made compatible with uranium in this way were then subjected to radiation by X-rays the dose of which was approximately 50kR at 120kV and 18mA. During this radiation, an aluminum filter having a thickness of 1.7mm was employed. The green algae treated in this way were subsequently poured onto agar-plates which contained the above mentioned nutrient solution as well as 500mg/1 uranium. The colonies thus formed were individually inoculated. The thus obtained single-celled cultures were tested as to their capability of receiving uranium. To this end, the above mentioned formed colonies are again inserted into a nutrient solution of the above mentioned composition and are further cultivated in this manner. The cultures of uranium compatible one-celled algae were tested as to ability to take on or pick up uranium by inserting the same into sea water which contained a concentration of less that 6ppb uranium. This solution was changed daily for ten days. It was found that the centrifuged off algae had a uranium content which is higher by a factor of 1,000 than the uranium content of the medium into which the uranium compatible algae were inserted.

It is, of course, to be understood that the present invention is, by no means, limited to the specific example set forth above, but also comprises any modifications within the scope of the appended claims.

It may also be mentioned that by "earth extract" is to be understood treated humus soil. More specifically, 1kg of humus soil has been mixed with 1 liter of water and subjected to a temperature of 100° C. for 2 hours, whereupon the water is filtered off. The thus obtained substance is the earth extract involved.

With regard to the process step of subjecting the algae to an X-ray radiation, the radiation time may vary from a few seconds to a few hours, depending on the algae and other circumstances involved. The main point is that the total dose of X-ray radiation administered to the algae is 50kR or about 50kR.

What we claim is:

1. A method of preparing a matrix comprising in combination mutants for single cell green algae to be cultivated compatible with uranium and suitable for extracting uranium dissolved in sea water, which includes the steps of: introducing the algae into a sterilized nutrient solution adjusted to an acidity of ph 6, and formed of 3.8 grams sea salt, 0.03 grams of $NH_4NO_3$ as well as 5ml earth extracts in 100 ml water, introducing in steps into the thus obtained solution uranium in the form of uranylnitrate until the quantity of uranium has been enriched to 250mg/l, subjecting the algae to X-ray radiation at a dose of approximately 50 kR, pouring the algae onto agar plates formed by employing a solution of 3.8 grams sea salt and 0.03 grams of $NH_4NO_3$ and 5ml earth extracts in 100 ml water, inoculating the thus forming colonies individually and further cultivating the same in a nutrient solution formed by the solution of 3.8 grams sea salt and 0.03 grams $NH_4NO_3$ and 5ml earth extracts in 100 ml water.

2. A method of extracting uranium from sea water comprising passing uranium-containing sea water through the matrix prepared by the method of claim 1.

3. A uranium-compatible matrix prepared by the method of claim 1.

* * * * *